United States Patent [19]
DeCampos et al.

[11] Patent Number: 6,086,633
[45] Date of Patent: *Jul. 11, 2000

[54] METHOD FOR PRESERVING ANIMAL HIDES

[75] Inventors: Rogerio B DeCampos, Sao Paulo, Brazil; Martin K Kemmerling, Clinton, Ind.

[73] Assignee: Eli Lilly and Company, Indianapolis, Ind.

[*] Notice: This patent is subject to a terminal disclaimer.

[21] Appl. No.: 09/284,692

[22] PCT Filed: Oct. 17, 1996

[86] PCT No.: PCT/US96/16840

§ 371 Date: Jul. 2, 1999

§ 102(e) Date: Jul. 2, 1999

[87] PCT Pub. No.: WO98/16663

PCT Pub. Date: Apr. 23, 1998

[51] Int. Cl.[7] ............... C14C 1/00; C14C 1/02; A01N 43/00
[52] U.S. Cl. ............ 8/94.18; 252/8.57; 424/404; 424/405; 424/409; 424/417; 424/489; 424/457; 424/458; 424/438; 514/460; 514/772
[58] Field of Search ............ 8/94.18; 252/8.57; 424/404, 405, 409, 417, 489, 457, 458, 438; 514/460, 772

[56] References Cited

U.S. PATENT DOCUMENTS

| | | | |
|---|---|---|---|
| 3,073,665 | 1/1963 | Williams | 8/94.18 |
| 4,935,031 | 6/1990 | Muench et al. | 8/94.18 |
| 5,252,561 | 9/1995 | Hornykiewytsch et al. | 514/23 |
| 5,273,752 | 12/1993 | Ayer et al. | 424/438 |
| 5,277,912 | 1/1994 | Lowe et al. | 424/438 |
| 5,624,710 | 4/1997 | Grabitz | 427/212 |
| 5,874,103 | 2/1999 | Moore et al. | 424/438 |

FOREIGN PATENT DOCUMENTS

| | | | |
|---|---|---|---|
| 0 671 174 | 9/1995 | European Pat. Off. | A61K 33/04 |
| WO 97/03650 | 2/1997 | WIPO . | |
| WO 97/16195 | 5/1997 | WIPO . | |

OTHER PUBLICATIONS

Database WPI, Section Ch, Week 198640 Derwent Publications Ltd, London Aug. 20, 1986, Abstract.

*Primary Examiner*—Alan Diamond
*Attorney, Agent, or Firm*—Frederick D. Hunter

[57] ABSTRACT

Compositions and methods for preserving untanned animal hides, wherein the compositions comprise 50–95% (w/w) of a polyether antibiotic and 5–25% (w/w) of a surface-acting agent. In these compositions, greater than 90% of the polyether antibiotic has a particle size of less than 25 microns, and the surface-acting agent is present in an amount that is effective to disperse the polyether antibiotic uniformly in an aqueous suspension.

27 Claims, No Drawings

METHOD FOR PRESERVING ANIMAL HIDES

This application is a 371 of PCT/US96/16840 filed Oct. 17, 1996.

BACKGROUND OF THE INVENTION

This invention relates to compositions and methods for preserving animal hides, in particular, protecting them against degradation resulting from microbiological growth.

Animal hides received by tanneries in excellent condition can be used for valuable end products and sold at a premium as compared to lesser quality hides. However, prior to arriving at a tannery, freshly stripped hides are typically washed and stored; during this period, such hides are susceptible to decomposition by microorganisms. Microbial growth on the hide surface and within the hide and blood vessels may cause irreparable damage resulting in lower quality hides having reduced value. Damaged hides may display holes or darkened areas, reduced hide strength, and altered stretching characteristics. Hair slippage, color, and integrity, all measures of hide quality, may also be adversely affected by microbial growth.

A variety of agents have been used for preserving hide quality but numerous detrimental effects are associated with their use. The oldest and most widely used preservation process is treatment of the hides with sodium chloride. Salt reduces the water content of the hides creating an adverse environment for microbial growth. Concentrated salt solutions also have a certain bactericidal activity. Typically, 0.3–0.6 kg sodium chloride per kg of wet hide is added to control microbial growth. However, the addition of such agents as sodium chloride also provokes hide shrinkage that may be considered a loss. Moreover, the sodium chloride is corrosive to equipment and its use results in significant, negative environmental impact on discharge or additional expense when removed prior to discharge.

The rot-preventing effect of salt can be enhanced by the addition of chemical biocidal or bactericidal agents, thereby reducing the amount of salt required. Such additives include, for example, naphthalene, p-chloro-m-creosol, sodium silicofluoride, ortanotin compounds, chlorinated phenols, pyridine derivatives, quaternary ammonium compounds, zinc salts, monochloroacetic acid, and many others. However, all of these additives require the concomitant use of a relatively high quantity of salt.

Likewise, antibiotics, such as tetracyclines, streptomycin, and penicillin, have also been proposed for use in preserving hides by inclusion in a hot brine solution. This method also contemplates optionally injecting the antibiotic into the animal prior to slaughter followed by immersion in the antibiotic-containing hot brine solution.

Numerous attempts to develop salt-free preservation processes have been largely unsuccessful. Such attempts include drying, solvent dehydration, bactericidal treatment, irradiation, and cooling. These processes have been generally unreliable for a variety of reasons, e.g., damage to the hides, toxicological and environmental safety problems, limited effectiveness, and/or economically unviable.

The present invention addresses the need to preserve hides without damage and eliminate the adverse economic and environmental impacts associated with the use of other agents and processes.

SUMMARY OF THE INVENTION

The present invention provides a novel composition useful for preserving untanned animal hides comprising:

(a) 50–95% (w/w) of a polyether antibiotic wherein greater than 90% of the particles are less than 25 microns in size, and (b) 5–25% (w/w) of a surface-acting agent effective to uniformly disperse the polyether antibiotic in an aqueous suspension.

Accordingly, the present invention also provides a method for preserving untanned animal hides comprising contacting the hides with an aqueous suspension containing at least 0.1 g/l of the above described composition, preferably 1–10 g/l of the composition, and especially 1, 5, or 10 g/l.

It is preferred that the composition and method comprise a polyether antibiotic having a median particle size of about 7–10 microns.

Moreover, it is preferred that the composition comprise 70–90% (w/w) of a polyether antibiotic, especially 80%. Likewise, it is preferred that the composition comprise 5–20% (w/w) of a surface-acting agent, more preferably 10–20%, especially about 12–17%.

Thus, an especially preferred method comprises, for example, contacting animal hides with 5 g/l of a composition that contains 80% polyether antibiotic and 12–17% surface-acting agent, that is, 4 g/l polyether antibiotic and 0.6–0.85 g/l surface-acting agent in the final hide-preserving suspension. Such a method is particularly applicable for use when the hides are to be sprayed with the suspension. Suspensions containing 1 g/l of the composition (0.8 g/l polyether antibiotic; 0.12–0.17 g/l surface-acting agent) are also particularly suited for use when the hides are to be immersed in the suspension.

DETAILED DESCRIPTION OF THE INVENTION

The present invention relates to a novel composition comprising bacteriostatic or bactericidal concentrations of polyether antibiotics having a reduced particle size and amounts of surface-acting agents effective to uniformly disperse the polyether antibiotic in an aqueous suspension, such composition being useful for preserving untanned animal hides.

The composition of the current invention is desirable for use by hide removal and processing plants for a variety of reasons. The polyether antibiotic active agents are very stable compounds. They do not easily degrade over time or under high temperature, remaining active for many days under typical hide storage conditions. Polyether antibiotics are effective at low concentrations in hide processing, thereby minimizing the quantities being delivered to waste treatment systems and keeping the cost of such treatment low. Moreover, aerobic waste treatment systems are not affected by the antibiotic activity, presumably since the polyether antibiotics are partially or completely degraded under aerobic conditions. These characteristics provide the opportunity to process animal hides free of salt.

Experiments conducted on freshly removed hides, using compositions of the current invention containing sodium monensin crystals that had been air milled to a reduced particle size and mixed with sodium lauryl sulfate, demonstrated that the antimicrobial activity of such compositions was adequate to preserve hide quality for a time sufficient to allow processing and transport to a tanning facility. In this way the detrimental effects associated with sodium chloride use were avoided. Moreover, the effectiveness of such compositions on control of odor, hair loosening (slippage), hide color, and soluble nitrogen concentration also demonstrated their usefulness for hide processing. Significantly, compositions of the current invention are better able to preserve hides than currently available commercial chemical antimicrobial agents when compared to the industry's reported experience with, and the advertised claims of, such products.

It will be recognized that various polyether antibiotics will likewise be suitable for use in the current invention. Examples of suitable polyether antibiotics include monensin, lonomycin, ionomycin, nigericin, grisorixin, dianemycin, lenoremycin, antibiotic X206, alborixin, septamycin, antibiotic A204, compound 47224, mutalomycin, salinomycin, lasalocid, isolasalocid A, lysocellin, tetronasin, echeromycin, antibiotic X14766A, antibiotic A23187, antibiotic A32887, compound 51532, K41, semduramycin, narasin, maduramycin, and laidlomycin. The use of monensin in the current invention is preferred, and the use of sodium monensin is especially preferred. The skilled artisan will recognize that other polyether antibiotics are also suitable for use in the current invention.

The current composition may be applied to the hides by direct application including dipping or immersing the hides in a suspension of the current composition, sprinkling or spraying the suspended composition onto the hides, or any other method of application whereby the composition comes into contact with the hides. Concentrations of composition of at least 0.1 g/l in the treatment suspension are effective. Given the designated range of active polyether antibiotic of 50–95% (w/w) that may be included in the composition, the concentration of polyether antibiotic in a hide-preserving suspension using 0.1 g/l of composition would be 0.05–0.095 g/l. The use of 1–10 g/l of composition is preferred (0.5–9.5 g/l of polyether antibiotic). The use of 1, 5, or 10 g/l of composition (0.5–0.95 g/l, 2.5–4.75 g/l, or 5–9.5 g/l polyether antibiotic, respectively) is further preferred.

Since the polyether antibiotics are only slightly soluble in the aqueous environment typically utilized for animal hide processing, in order to achieve effectiveness, the polyether antibiotic must be uniformly dispersed in an aqueous suspension. According to the current invention, the polyether antibiotic may dispersed by the addition of a broad range of surface-acting agents, including, for example, various fatty acids, linear alkyl sulfonates, and alkyl benzene sulfonates. Specific surface-acting agents which are suitable for use in the current invention include, for example, sodium lauryl sulfate, ammonium lauryl sulfate, triethanolamine lauryl sulfate, sodium caprylic acid, sodium cholic acid, sodium lauryl ether sulfate, ammonium lauryl ether sulfate, lauryl dimethyl amine oxide, sodium N-lauroylsarcosin, benzalkonium chloride, cetylpyridinium chloride, various polyoxyethylene ethers, and various polyoxyethylenesorbitans. Compositions having 10–20% (w/w) surface-acting agent are preferred; those having about 12–17% surface-acting agent are more preferred. Sodium lauryl sulfate is a preferred surface-acting agent for the current invention.

Uniform dispersion is also affected by particle size. Polyether antibiotics having a particle size distribution wherein at least 90% of the particles are less than 25 microns may be used in the current invention. A distribution of particles having a median size of about 7–10 microns is preferred. For purposes of the current invention, all measurements of particle size were done according to laser diffraction technology and reported as diameters.

Of course, the effectiveness of suspensions created by using the current compositions is dependent upon the interaction of particle size and the concentration of surface-acting agent. As particle size is reduced, the requirement for a surface-acting agent also decreases. It is a matter of skill in the art to determine effective ratios of polyether antibiotic to surface-acting agent for any given particle size. Relative amounts of polyether antibiotic and surface-acting agents expressed as percents in this disclosure are calculated on a weight basis (w/w).

The fermentation of organisms responsible for production of the various polyether antibiotics and subsequent isolation steps typically result in polyether antibiotic crystals of greater than 20 microns in size (generally 20–50 microns), and having a purity of 80–98%. Thus, the isolated crystals may contain 2–20% undefined inert matter. This crystalline material may be processed according to a number of known procedures to reduce the particle size to the required specifications. Air milling is particularly suited to micronize the particles to the extent necessary.

The processed material is then mixed directly with the surface-acting agent by any means suitable thereby generating the current compositions. Mechanical mixing or air mixing, for example, may be used in the current invention.

For ease in use, the composition of the current invention can be formulated into a package that can be added to an aqueous phase to generate a suspension containing the desired concentrations of polyether antibiotic and surface-acting agent. For example, it is particularly contemplated that a 100 g package containing 80 g (80% (w/w)) crystalline monensin and approximately 12–17 g (12–17% (w/w)) sodium lauryl sulfate be prepared. A 1000 g package containing 800 g crystalline monensin and 120–170 g sodium lauryl sulfate is also contemplated. For particular convenience, the packaging material may be made of water soluble materials such that the package may be added to the aqueous diluent without having to separately prepare the composition thereby avoiding contact with the ingredients.

The present invention is contemplated as being useful in a wide variety of situations, including, but not limited to, the preserving of untanned hides from the following species: bovine (including Bos taurus and Bos indicus animals), porcine, ovine, caprine, equine, fish (including eel), avian (including ostrich, emu, and other fowl), reptiles (including alligators, snakes and lizards), fur animals (including rabbit, raccoon, beaver, muskrat and other rodents) and other exotic species such as yak, vicunas, llamas, camels, or any other type of animal hide used in the manufacture of leather or production of pelts for use in taxidermy or decoration. Thus, any animal hide that can be tanned for leather, taxidermy, decoration or other uses can be processed in accordance with the present invention.

The following examples are intended for illustrative purposes and are not intended and should not be construed as limiting the invention in any way.

EXAMPLE 1

Composition Preparation

Sodium monensin crystals (92.7% pure) were air milled. The air mill device used was typical in that the crystals were introduced into a high speed air stream that conveyed the crystals with high turbulence into an impact and classifying chamber. The crystals were reduced by interparticular impact and attrition. The reduced particles are expelled and the oversize particles are retained for further milling. After milling the monensin had a particle size distribution as follows:

| Particle Size (microns) | % of Sample less than size indicated |
| --- | --- |
| 1.09 | 5 |
| 1.68 | 10 |
| 3.45 | 25 |
| 7.20 | 50 |
| 22.34 | 99 |
| 28.46 | 95 |
| 52.50 | 100 |

172.6 Kg of the milled crystals were mixed in a blender with 27.4 kg of sodium lauryl sulfate (industrial grade) resulting in a composition containing 80% sodium monensin and 13.7% sodium lauryl sulfate.

The composition s o prepared was then used for a number of experimental trials described in the following examples.

EXAMPLE 2

Impact on Hide Quality

Compositions prepared as in Example 1 were suspended in water with stirring at varying concentrations. Freshly harvested hides were then immersed in tanks containing the various suspensions (Tank). Other fresh hides were sprayed with approximately 3 liters/hide of the various suspensions (Spray). The monensin treated hides were then stacked and stored at ambient temperature.

Preservation of monensin-treated hides was evaluated at various times by reference to parameters typically used to subjectively assess hide quality, such as hair slippage, odor, and color. These indicators were compared to (1) those for hides receiving no antimicrobial treatment, but which were stored at refrigerated temperatures, and (2) untreated hides that were stored under the same conditions as the treated hides.

The results are presented in Table 1.

TABLE 1

| Storage | | | | Treatment | | | | | |
| --- | --- | --- | --- | --- | --- | --- | --- | --- | --- |
| Time (hrs) | Quality Parameter | Refrig. Temp. | Ambient Temp. | Tank 0.1 g/l | Tank 0.5 g/l | Tank 1 g/l | Spray 1 g/l | Spray 5 g/l | Spray 10 g/l |
| 24 | Hair Slip | + | + | + | + | + | + | + | + |
|  | Odor | + | ± | ± | ± | + | + | + | + |
|  | Color | + | + | + | + | + | + | + | + |
| 48 | Hair Slip | + | − | + | + | + | + | + | + |
|  | Odor | + | ± | ± | ± | + | + | + | + |
|  | Color | + | − | ± | ± | ± | + | + | + |
| 72 | Hair Slip | + | − | + | − | − | ± | + | + |
|  | Odor | + | − | ± | ± | ± | ± | + | + |
|  | Color | + | − | − | − | − | ± | + | + |
| 96 | Hair Slip | + | − | − | − | − | − | ± | ± |
|  | Odor | + | − | − | − | − | ± | ± | + |
|  | Color | + | − | − | − | − | − | ± | + |
| 192 | Hair Slip | + | − | − | − | − | − | − | ± |
|  | Odor | + | − | − | − | − | − | − | ± |
|  | Color | + | − | − | − | − | − | − | ± |

+ No degradation detected
± Initial stages of degradation detected
− Degradation detected

EXAMPLE 3
Impact on Hide Quality

Freshly harvested hides were either immersed in tanks containing suspensions of the hide-preserving compositions (Tank) or treated with sprays of the suspensions (Spray) as in Example 2 at concentrations indicated in Table 2. The monensin-treated hides were again stacked and stored at ambient temperature.

Hide quality parameters for the treated hides were compared to those for refrigerated, untreated hides. The results are presented in Table 2.

TABLE 2

| | | | Treatment | | |
| --- | --- | --- | --- | --- | --- |
| Storage Time | Test | Refrig. Control | Tank 0.1 g/l | Tank 5 g/l | Spray 5 g/l |
| 24 hrs | Hair Slip | + | + | + | + |
|  | Odor | + | + | + | + |
|  | Color | + | + | + | + |
| 48 hrs | Hair Slip | + | + | + | + |
|  | Odor | + | + | + | + |
|  | Color | + | + | + | + |
| 72 hrs | Hair Slip | + | + | + | + |
|  | Odor | + | + | + | + |
|  | Color | + | + | + | + |
| 96 hrs | Hair Slip | + | + | + | + |
|  | Odor | + | + | + | + |
|  | Color | + | + | + | + |
| 192 hrs | Hair Slip | + | ± | ± | ± |
|  | Odor | + | ± | ± | ± |
|  | Color | + | ± | ± | ± |

+ No degradation detected
± Initial stages of degradation detected
− Deterioration detected

EXAMPLE 4

Production-Scale Hide Treatment

Three separate large-scale plant trials (approximately 3.2 metric tons of hide) were conducted in two different leather processing plants. Fresh hides were immersed in suspension (prepared as in Examples 2 and 3) of high-preserving composition at a concentration of 1 g/l and subjected to mild agitation. Hide degradation was measured using the same subjective tests as Examples 2 and 3 for a 120 hours. The results are shown in Table 3.

TABLE 3

| Trial # | Storage Temp | Hours of Storage | | | |
|---|---|---|---|---|---|
| | | 48 | 72 | 96 | 120 |
| 1 | 17–29 C. | + | ND | ND | ND |
| 2 | 12–22 C. | + | + | + | ND |
| 3 | 13–23 C. | + | + | + | Hair slip detected |

+ No degradation detected
± Initial stages of degradation detected
− Degradation detected
ND Test Not Done

EXAMPLE 5

Effect on Soluble Nitrogen Concentration

Degradation of hides is related to protein metabolism. Thus, increases in the measure of soluble nitrogen compared to the total nitrogen present is an indication of degradation. Table 4 illustrates the effect of the current composition upon protein degradation in hides stored at ambient temperature for up to 96 hours compared to untreated controls stored at either refrigerated or ambient temperature. Hides were either immersed (Tank) or sprayed (Spray) with suspensions of hide-preserving composition at the concentrations indicated in Table 4. Soluble nitrogen concentrations were measured at 24 hour intervals.

TABLE 4

| Treatment | Composition (g/l) | Time of Storage (hrs) | | | | |
|---|---|---|---|---|---|---|
| | | 0 | 24 | 48 | 72 | 96 |
| Refrig. Untreated | — | 0.6% | ND | ND | ND | ND |
| Ambient Untreated | — | 0.6% | 1.1% | 2.9% | 4.8% | 6.9% |
| Tank | 0.1 | 0.6% | 1.0% | ND | 3.2% | ND |
| Tank | 0.5 | 0.6% | 1.2% | 1.7% | 3.1% | ND |
| Tank | 1.0 | 0.6% | 1.2% | ND | 1.7% | 3.1% |
| Spray | 1.0 | 0.6% | ND | ND | 3.3% | ND |
| Spray | 5.0 | 0.6% | ND | 1% | 1% | 1.9% |
| Spray | 10.0 | 0.6% | ND | ND | ND | 1.0% |

ND Test Not Done

We claim:

1. A composition for preserving untanned animal hides comprising:
   (a) 50–95% (w/w) of a polyether antibiotic wherein greater than 90% of the antibiotic has a particle size of less than 25 microns, and
   (b) 5–25% (w/w) of a surface-acting agent effective to uniformly disperse the polyether antibiotic in an aqueous suspension.

2. The composition of claim 1 comprising 70–90% of the polyether antibiotic.

3. The composition of claim 1 comprising about 80% of the polyether antibiotic.

4. The composition of claim 1 or 3 wherein the polyether antibiotic is sodium monensin.

5. The composition of claim 1 or 3 comprising 10–20% (w/w) of the surface-acting agent.

6. The composition of claim 1 or 3 comprising about 12–17% (w/w) of the surface-acting agent.

7. The composition of claim 1 or 3 wherein the surface-acting agent is sodium lauryl sulfate.

8. The composition of claim 4 comprising about 12–17% (w/w) sodium lauryl sulfate as the surface-acting agent.

9. The composition of claim 1 or 3 wherein the polyether antibiotic has a median particle size of about 7–10 microns.

10. The composition of claim 8 wherein the polyether antibiotic has a median particle size of about 7–10 microns.

11. A method for preserving untanned animal hides comprising contacting the hides with an aqueous suspension containing at least 0.1 g/L of a composition comprising
    (a) 50–95% (w/w) of a polyether antibiotic wherein greater than 90% of the antibiotic has a particle size of less than 25 microns, and
    (b) 5–25% (w/w) of a surface-acting agent effective to disperse the polyether antibiotic uniformly in an aqueous suspension.

12. A method of claim 11 wherein the polyether antibiotic comprises about 80% of the composition.

13. A method of claim 11 wherein the suspension contains 1–10 g/L of the composition.

14. A method of claim 12 wherein the suspension contains 1–10 g/L of the composition.

15. A method of claim 11 wherein the polyether antibiotic is monensin.

16. The method of claim 13 wherein the polyether antibiotic has a median particle size of about 7–10 microns.

17. A method of claim 15 wherein the polyether antibiotic has a median particle size of about 7–10 microns.

18. A method of claim 15 wherein the surface-acting agent is sodium lauryl sulfate and comprises 12–17% of the composition.

19. A method of claim 15 wherein the aqueous suspension contains 1–10 g/L of the composition.

20. The method of claim 13 wherein the suspension contains 1 g/L, 5 g/L, or 10 g/L of the composition.

21. The method of claim 14 wherein the suspension contains 1 g/L, 5 g/L, or 10 g/L of the composition.

22. The method of claim 14 wherein the polyether antibiotic has a median particle size of about 7–10 microns.

23. The method of claim 18 wherein the polyether antibiotic has a median particle size of about 7–10 microns.

24. A kit comprising:
    (a) about 80% (w/w) of a polyether antibiotic wherein greater than 90% of the antibiotic has a particle size of less than 25 microns; and
    (b) 12–17% (v/v) of a surface-acting agent, wherein the polyether antibiotic and the surface-acting agent are packaged in a container, which is optionally water soluble.

25. A kit of claim 24 wherein the polyether antibiotic is sodium monensin having a median particle size of about 7–10 microns and the surface-acting agent is sodium lauryl sulfate.

26. A kit of claim 25 weighing a total of 1000 grams.

27. A kit of claim 25 weighing a total of 100 grams.

* * * * *